United States Patent
Doll et al.

(10) Patent No.: US 7,850,713 B2
(45) Date of Patent: Dec. 14, 2010

(54) DEVICE FOR FIXING AND TENSIONING AT LEAST ONE PULLING THREAD FOR APPLYING A NEOVAGINA

(75) Inventors: Frank Doll, Talheim (DE); Christian Walter, Emmingen-Liptingen (DE)

(73) Assignee: Karl Storz GmbH & Co. KG (DE)

( * ) Notice: Subject to any disclaimer, the term of this patent is extended or adjusted under 35 U.S.C. 154(b) by 1269 days.

(21) Appl. No.: 11/410,215

(22) Filed: Apr. 24, 2006

(65) Prior Publication Data

US 2006/0229676 A1 Oct. 12, 2006

Related U.S. Application Data

(63) Continuation of application No. PCT/EP2004/011965, filed on Oct. 22, 2004.

(30) Foreign Application Priority Data

Oct. 24, 2003 (DE) ................. 103 49 953

(51) Int. Cl.
A61B 17/04 (2006.01)
(52) U.S. Cl. .......................... 606/232; 606/233; 600/37
(58) Field of Classification Search .................. 600/37; 606/148, 213–221, 233
See application file for complete search history.

(56) References Cited

U.S. PATENT DOCUMENTS

| 3,650,274 A | | 3/1972 | Edwards et al. ............. 128/335 |
| 3,695,271 A | * | 10/1972 | Chodorow .................. 606/233 |
| 4,667,675 A | * | 5/1987 | Davis ......................... 606/233 |
| 4,773,421 A | * | 9/1988 | Davis ......................... 606/233 |
| 5,127,412 A | * | 7/1992 | Cosmetto et al. ............ 128/898 |
| 5,276,991 A | * | 1/1994 | Stotesbury et al. ............. 43/24 |
| 5,649,960 A | * | 7/1997 | Pavletic ...................... 606/216 |
| 5,855,591 A | * | 1/1999 | Bierman ...................... 606/232 |

(Continued)

FOREIGN PATENT DOCUMENTS

DE 36 16 957 11/1987

(Continued)

OTHER PUBLICATIONS

Kaloo P and Cooper M. Laparoscopic-assisted Vecchietti procedure for creation of a neovagina: an analysis of five cases. Australian and New Zealand Journal of Obstetrics and Gynaecology 42 (3): 307-310, 2002).*

(Continued)

Primary Examiner—Charles A Marmor, II
Assistant Examiner—Catherine E. Burk
(74) Attorney, Agent, or Firm—St. Onge Steward Johnston & Reens LLC

(57) ABSTRACT

A device for fixing and tensioning at least one pulling thread for applying a neovagina comprises a base body on which at least one fixing element is arranged for fixing the at least one pulling thread with tensioning. The fixing element is able to turn about an axis of rotation in order to tension the at least one pulling thread, and a blocking device is provided for the fixing element, by means of which blocking device the fixing element can be blocked at least in a direction of rotation opposite to the direction of rotation for tensioning the at least one pulling thread.

16 Claims, 6 Drawing Sheets

U.S. PATENT DOCUMENTS 6,120,525 A     9/2000   Westcott ...................... 606/216
6,446,936 B1 *   9/2002   Ostrobrod ................... 254/368

FOREIGN PATENT DOCUMENTS

| | | |
|---|---|---|
| DE | 42 43 492 | 9/1993 |
| EP | 0 615 725 | 9/1994 |
| WO | WO 99/35974 | 7/1999 |

OTHER PUBLICATIONS

Borruto F, Chasen ST, Chervenak FA, and Fedele L. The Vecchietti procedure for surgical treatment of vaginal agenesis: comparison of laparoscopy and laparotomy. International Journal of Gynecology & Obstetrics 64: 153-158, 1999).*

Specialist article in German language by J. Keckstein "Anlegen einer Neovagina (nachVecchietti)", pp. 332-338, 7 pages.

International Search Report; Feb. 3, 2005; 3 pages.

International Preliminary Report on Patentability, 5 pages.

* cited by examiner

DEVICE FOR FIXING AND TENSIONING AT LEAST ONE PULLING THREAD FOR APPLYING A NEOVAGINA

CROSS-REFERENCE TO RELATED APPLICATIONS

The present application is a continuation of pending International Patent Application PCT/EP2004/011965 filed on Oct. 22, 2004 which designates the United States, and which claims priority of German patent application No. 103 49 953.9 filed on Oct. 24, 2003.

BACKGROUND OF THE INVENTION

The invention relates to a device for fixing and tensioning at least one pulling thread for applying a neovagina.

Such a device is known from the specialist article, in German, by J. Keckstein "Anlegen einer Neovagina (nach Vecchietti)" [Applying a neovagina (Vecchietti method)] in: "Die endoskopischen Operationen in der Gynäkologie" [Endoscopic operations in gynecology], publishers J. Keckstein, Hucke, Urban and Fischer Verlag 2001, 1st edition, pages 332-338. This specialist article, specifically in respect of the method described therein for applying a neovagina, is incorporated into the present application by reference.

A device of the abovementioned type is used in the context of a surgical procedure for applying a neovagina. Applying a neovagina is understood as meaning a vaginal reconstruction which is performed in the absence of a vaginal structure, the latter being a malformation of the female genitalia, as seen in Mayer-Rokitansky-Küster syndrome and in cases of testicular feminization.

The surgical procedure for vaginal reconstruction was originally performed by laparotomy and later by laparoscopy, i.e. by an endoscopic approach.

The surgical principle involved in applying a neovagina lies in stretching the vaginal dimple. A plastic olive or phantom, described in the document 36 16 957 A1 for example, and connected to two pulling threads, is used to apply continuous pressure on the vaginal dimple, and, in this way, a neovagina is stretched or formed within a period of days. The two pulling threads of the plastic olive or phantom are guided from the direction of the vaginal dimple using a straight awl, used to perforate the vaginal dimple, in the intraperitoneal direction, i.e. into the abdominal space, and then pulled with a curved awl in the retroperitoneal direction to a position in front of the abdominal wall. In front of the abdominal wall, the two pulling threads are then fixed to a device of the aforementioned type and tensioned, so that the pulling threads exert a continuous tensile force on the plastic olive or phantom, as a result of which the olive or phantom then exerts a continuous stretching pressure on the vaginal dimple.

The device known from the aforementioned specialist article in German, and used for fixing and tensioning the two pulling threads, comprises an approximately rectangular flat base body, a fixing element being arranged on each of its two narrow sides, in each case for one of the two pulling threads. Each fixing element is assigned a spring on which the corresponding pulling thread is attached. The springs have the function of attenuating sudden changes in pulling force caused by movements of the body. The two fixing elements comprise rotary screws by means of which the ends of the pulling threads are clamped and thus fixed. No tensioning of the pulling threads is permitted by way of the fixing elements, and instead the pulling threads of this device have to be tightened by hand with the rotary screw loosened, so that, before each re-tensioning, the rotary screw of the fixing element is first loosened and the pulling thread is tightened by hand, and then the rotary screw is tightened again in order to fix the pulling thread. The tensioning and fixing of the pulling threads is therefore relatively time-consuming and awkward.

In the context of the method for applying a neovagina, however, frequent re-tensioning of the pulling threads is necessary, because the plastic olive or phantom is of course intended to continuously exert pressure on the vaginal dimple and in so doing stretch the latter.

A further disadvantage of this known device is that a separate fixing element is present for each pulling thread, with the result that the two pulling threads have to be tensioned and fixed after one another and independently of one another. This not only increases the time needed for tensioning and fixing the pulling threads, but also makes it difficult to obtain uniform tensioning of the two pulling threads. Uniform tensile stressing of the two pulling threads is, however, important, because, if the tensile stressing is not uniform, only one of the pulling threads exerts a pulling force and is therefore prone to tear, and the direction of tensile force on the olive is in some cases not optimal if only one thread is pulling.

The same specialist article in German describes another device for fixing and tensioning the two pulling threads. This known device comprises two separate fixing elements, i.e. they are not arranged and secured on a common base body. Each fixing element comprises a circular base plate on which a helical spring with spaced-apart windings is arranged, this being adjoined at the top by a further circular plate on which a fixing screw is arranged for fixing a pulling thread. With these fixing elements too, the tensioning of the respective pulling thread has to be done by pulling and holding the end of the pulling thread by hand and then screwing the fixing screw tight, which, in the same way as in the known device described above, is time-consuming and awkward. In addition, this known device entails the aforementioned disadvantage that the two pulling threads cannot be tensioned simultaneously, as a result of which a uniform tensioning of the two pulling threads is likewise not possible in a controlled manner.

SUMMARY OF THE INVENTION

The object of the invention is in the first instance to develop a device of the type mentioned at the outset for fixing and tensioning at least one pulling thread for applying a neovagina, and to develop it in such a way that the procedure for fixing and tensioning the at least one pulling thread is made easier.

According to an aspect of the invention, a device for fixing and tensioning at least one pulling thread for applying a neovagina is provided, comprising a base body, at least one fixing element arranged on the base body for fixing the at least one pulling thread and turnable about an axis of rotation for tensioning the at least one pulling thread by rotating the at least one fixing element in a first direction of rotation about the axis of rotation, and a locking device for locking the at least one fixing element at least in a second direction of rotation opposite the first direction of rotation.

According to another aspect of the invention, a device for fixing and tensioning at least one pulling thread for applying a neovagina is provided, comprising a base body, at least one fixing element arranged on the base body and turnable about an axis of rotation, the at least one fixing element being designed for jointly fixing the at least one pulling thread and at least one further pulling thread and tensioning the at least one pulling thread and the at least one further pulling thread by rotating the at least one fixing element in the direction of rotation about the axis of rotation.

In the device according to the invention, it is accordingly proposed that the fixing element serves not only for fixing the at least one pulling thread with tensioning, but also for the tensioning of the pulling thread, by means of the fixing element being able to turn about an axis of rotation, as a result of which the pulling thread can be tensioned by winding about a portion of the fixing element. Accordingly, in order to fix and tension the at least one pulling thread, the procedure used in the device according to the invention is the reverse of the known devices. In other words, in the device according to the invention, the pulling thread is first secured or fixed on the fixing element, and is thereafter tensioned by turning the fixing element.

Moreover, in the device according to the invention, it is proposed that the fixing element can be locked by means of a locking device at least in one direction of rotation, which is the opposite to the direction of rotation for tensioning the pulling thread. Therefore, when the desired tensioning of the pulling thread has been obtained by turning the fixing element, this tensioning is then maintained by blocking the ability of the fixing element to turn, at least in the direction of rotation which is the opposite to the direction of rotation for tensioning the pulling thread.

For the re-tensioning of the at least one pulling thread that is necessary from time to time, the fixing element simply has to be turned further in the direction of rotation of the tensioning, as a result of which not only the initial tensioning, but also the re-tensioning of the at least one pulling thread is made very easy. It is also very easy, however, to release the tension of the pulling thread in cases where the tension of the pulling thread has been set too high, this being done by releasing the locking device, as a result of which, for releasing the tension of the pulling thread, the fixing element is allowed to turn in the direction of rotation which is the opposite to the direction of rotation for tensioning the pulling thread.

The device according to the invention thus permits very easily manageable and time-efficient fixing and tensioning of the at least one pulling thread, and in particular also very well-controlled adjustment of the tensioning of the pulling thread.

In a preferred embodiment, the locking device has a latching mechanism for locking the fixing element in the at least one direction of rotation.

This measure provides a structurally advantageously simple locking device for locking the fixing element, and one which in addition is also particularly simple in terms of its handling.

In this connection, it is preferable if the latching mechanism can be secured against undesired unlocking.

Since the device, in its use for applying a neovagina, is positioned for a long period of time on the patient's abdomen, this measure advantageously avoids the latching mechanism accidentally unlocking, for example while the patient is asleep, which means that it is possible to reliably avoid an undesired release of tension of the at least one pulling thread.

In another preferred embodiment, the fixing element has a circumferentially toothed wheel which, in order to lock the fixing element, interacts with a first catch element that can be brought into engagement with the toothing of the wheel.

The advantage of this embodiment of the fixing element is the advantage that a locking device for the fixing element in the form of a latching mechanism is created with only a small number of component parts and, therefore, at low cost. The catch element can, for example, be configured in the form of a peg or pin which can be moved into and out of engagement with the toothing of the wheel of the fixing element.

In this connection, it is preferable if the first catch element can be locked when it is in engagement with the toothing of the wheel.

By virtue of the first catch element being able to be locked when it is in engagement with the toothing of the wheel, a measure is effected, in a structurally advantageously simple manner, by which an undesired unlocking of the latching mechanism is avoided.

In another embodiment in this connection, in order to lock the first catch element, a second catch element is provided which can be shifted into the path of movement of the first catch element.

This measure ensures, in a structurally simple manner, that the latching mechanism is secured, in an operationally reliable manner, against undesired unlocking.

In another preferred embodiment, the fixing element has a slotted portion for receiving a portion of the at least one pulling thread, and a sleeve for clamping the pulling thread on the fixing element.

This measure has the advantage that the at least one pulling thread can be secured on the fixing element in a very easy way, by inserting a portion (usually the end) of the pulling thread into the slit and then fitting or screwing the sleeve onto the slotted portion of the fixing element, by which means the pulling thread is then securely clamped on the fixing element. It is particularly preferable if the sleeve can be fitted onto the slotted portion of the fixing element, since this fitting can be done very quickly. In the case of a sleeve that can be fitted in place, it is preferably able to be connected to the slotted portion of the fixing element in a rotationally fixed manner, for example locked onto it.

It is also preferable if the sleeve has a control wheel for turning the fixing element.

The advantage of this is that the sleeve at the same time represents the operating element for tensioning the at least one pulling thread, and therefore the number of component parts of the device according to the invention is further reduced.

In another preferred embodiment, the fixing element is assigned a spring whose first end is secured on the base body, and whose second end is configured for movable connection to the pulling thread and for deflecting the latter toward the fixing element.

This measure, which is known per se, has the advantage that the spring not only ensures a uniform tensioning of the at least one pulling thread, and pre-tensioning thereof, but also attenuates changes in tensile force that are caused by movement of the body.

In this connection, it is preferable if a movable guide roller is arranged at the second end of the spring.

Since the pulling thread is able to move relative to the second end of the spring in the event of the aforementioned changes in tensile force caused by a physical movement of the patient, this measure advantageously ensures a considerable reduction in friction between the pulling thread and the second end of the spring, which avoids tearing of the pulling thread due to abrasion.

In another preferred embodiment, a feed point for the pulling thread is present on the base body.

Providing a feed point for the pulling thread on the base body ensures that there is a well-defined and constant direction of tensile force of the pulling thread. The feed point can, for example, be configured in the form of a thread guide for the pulling thread.

In another preferred embodiment, the feed point is arranged in relation to the spring and to the fixing element in such a way that the pulling thread first runs from the feed point past the fixing element to the second end of the spring and from there to the fixing element.

In this connection, it is particularly preferable if the feed point is arranged in relation to the spring and to the fixing element in such a way that the pulling thread is deflected at the second end through approximately 180° toward the fixing element.

In another preferred embodiment, a movable guide roller is present at the feed point.

Here once again, as with the movable roller for the spring, the friction of the at least one pulling thread at the feed point is advantageously reduced, which avoids tearing of the pulling thread due to abrasion.

In another particularly preferred embodiment, the fixing element is designed for jointly fixing and tensioning the at least one pulling thread and at least one further pulling thread.

This measure now has the particular advantage that, with the device according to the invention, the normally two pulling threads present on the plastic olive or phantom can be tensioned simultaneously. This substantially reduces the effort involved in fixing and tensioning the two pulling threads by comparison to the known devices, because both pulling threads can be tensioned simultaneously with the one fixing element after they have been fixed to the fixing element. Moreover, this embodiment of the device according to the invention also permits a uniform tensioning of both pulling threads, which is possible only with difficulty in the known devices.

In one embodiment of the aforementioned measure, a feed point for the further pulling thread is provided on the base body, which feed point is arranged, in relation to the fixing element, opposite the feed point for the other pulling thread.

This now has the advantage, particularly in connection with the provided tensioning mechanism afforded by the rotatability of the fixing element, that both pulling threads can run from their feed points on approximately opposite sides of the base body to the fixing element, as a result of which the pulling threads run into the device at a distance from one another corresponding approximately to the spacing of the incisions in the abdominal wall of the patient from where the threads emerge from the abdomen. The tensile force direction is optimized in this way.

In another preferred embodiment, a further spring for the further pulling thread is arranged on the base body and, in relation to the fixing element, is arranged opposite the spring for the other pulling thread.

This measure results in what is overall a mirror-symmetrical arrangement of the springs and feed points of the two pulling threads in relation to the fixing element, as a result of which the device according to the invention can have a compact construction, i.e. takes up a small space on the patient's body. In addition, the tensile force distribution of the two pulling threads is likewise mirror-symmetrical in relation to the fixing element, as a result of which the position of the device on the patient's body is stable.

In another preferred embodiment, the device can be sterilized, in particular autoclaved.

The advantage of this is that the device is reusable, by which means the purchase costs of such a device in relation to its useful life are reduced.

Provision can also be made for the functional parts such as the fixing element, for example the springs and latching mechanism, to be removable from the base body, as a result of which the device according to the invention can be even better cleaned.

Further advantages and features will become evident from the following description and from the attached drawing.

It will be appreciated that the aforementioned features and those still to be explained below can be used not only in the respectively cited combination but also in other combinations or singly, without departing from the scope of the present invention.

BRIEF DESCRIPTION OF THE DRAWINGS

An illustrative embodiment of the invention is shown in the drawings and is described in more detail below with reference to this drawings, in which.

DETAILED DESCRIPTION OF THE INVENTION

In FIGS. 1 to 6, general reference number 10 labels a device for fixing and tensioning at least one pulling thread, in the present illustrative embodiment two pulling threads 12 and 14 (see FIG. 5), for applying a neovagina. Before the fixing and tensioning of the two pulling threads 12 and 14 is described, the structure of the device 10 will first be described in detail.

The device 10 comprises a base body 16 which, without implying any limitation, has substantially the shape of a rectangle. As will be seen from the figures, the corners of the rectangle are beveled, and the side edges of the base body 16 are preferably rounded. The base body 16 is substantially planar with a small thickness, and the underside (not shown) is smooth and flat.

Figure 3:
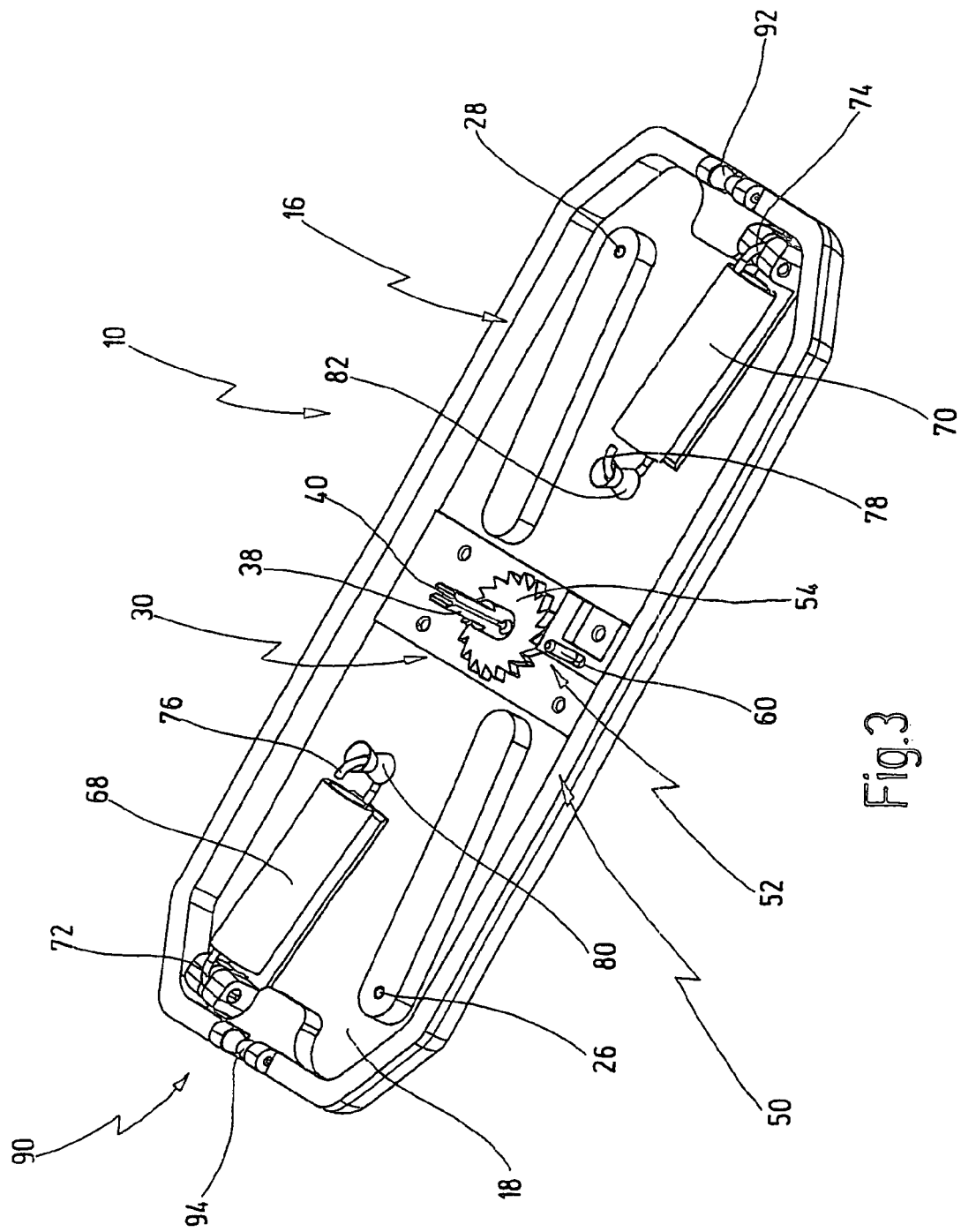
FIG. 3 shows the device from FIG. 1 in a perspective view from above, again with omission of some parts.

The base body 16 is formed by a bottom plate 18 and a top plate 20, the top plate 20 being able to be removed from the bottom plate 18. FIG. 3 shows the device 10 with the top plate 20 removed.

The top plate 20 is secured on the bottom plate 18 by means of two screws 22 and 24 (FIG. 1) which can be actuated by hand without a tool, and corresponding threaded bores 26 and 28 for the screws 22 and 24 are present in the bottom plate 18.

The bottom plate 18 in particular, and in the present case also the top plate 20, are made from a biocompatible material, such that the device 10 is tolerated by a patient's skin.

The device 10 as a whole can be sterilized, in particular autoclaved, and can thus be used several times for different patients.

Figure 4:
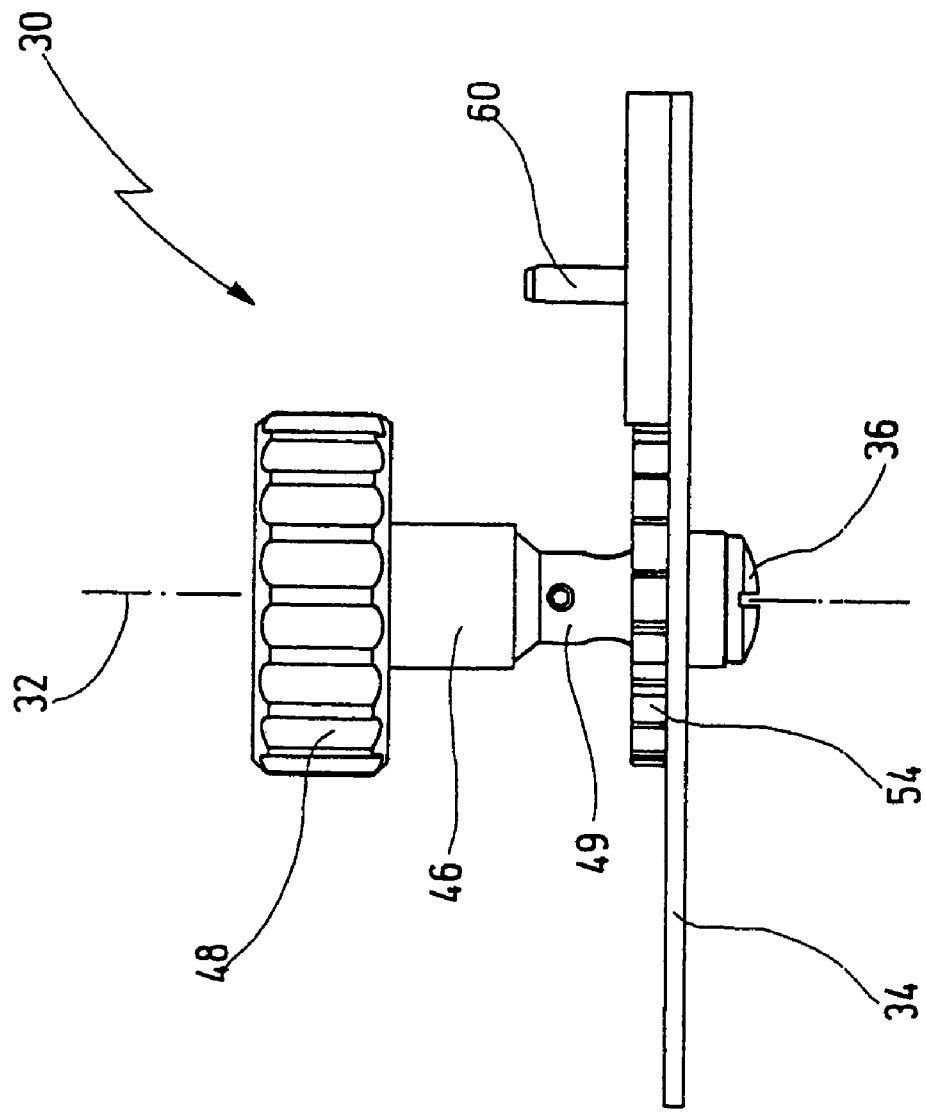
FIG. 4 shows a detail of the device from FIG. 1 in a side view, and on a larger scale compared to FIG. 1.

A fixing element 30 is arranged on the base body 16. FIG. 4 shows the fixing element 30 on a larger scale and in a side view.

A screw 36 secures the fixing element 30, rotatably about an axis of rotation 32, on an intermediate plate 34 connected to the bottom plate 18 (see FIG. 4). The screw 36 is accessible from the underside of the bottom plate 18.

The fixing element 30 has a slotted portion 38 which extends upward, as seen from the bottom plate 18, and which has a slit 40 (see FIG. 3). The slit 40 is used to receive a portion 42 or 44 (see FIG. 5) of the pulling threads 12 and 14, the portions 42 and 44 basically forming the ends of the pulling threads 12 and 14.

To clamp the portions 42 and 44 of the pulling threads 12 and 14 in the slit 40, the fixing element 30 also has a sleeve 46 which, in order to clamp the pulling threads 12 and 14, more precisely the portions 42 and 44 of the pulling threads 12 and 14, can be fitted onto the slotted portion 38 and can be locked thereon so as to be fixed in rotation with the slotted portion 38.

The sleeve 46 also has a control wheel 48 connected to it in one piece, the edge of the control wheel 48 being structured for better grip, for example knurled, said control wheel 48 serving as an actuating element for turning the fixing element 30.

As will be described later, both pulling threads 12 and 14 can be fixed by inserting the portions 42 and 44 into the slit 40 and fitting the sleeve 46 on the fixing element 30 and, thereafter, can be tensioned simultaneously and uniformly by turning the fixing element 30 about the axis of rotation 32. By means of the rotation of the fixing element 38, the pulling threads 12 and 14 wind round a section 49 of the slotted portion 38, as a result of which they are tensioned. In the present illustrative embodiment, the direction of rotation of the fixing element 30 for tensioning the pulling threads 12 and 14 is the clockwise direction. The fixing element 30 can also be turned in the counterclockwise direction, but the fixing element 30 can be locked at least in this direction of rotation, which is therefore the opposite of the direction of rotation for tensioning the pulling thread.

Figure 2:
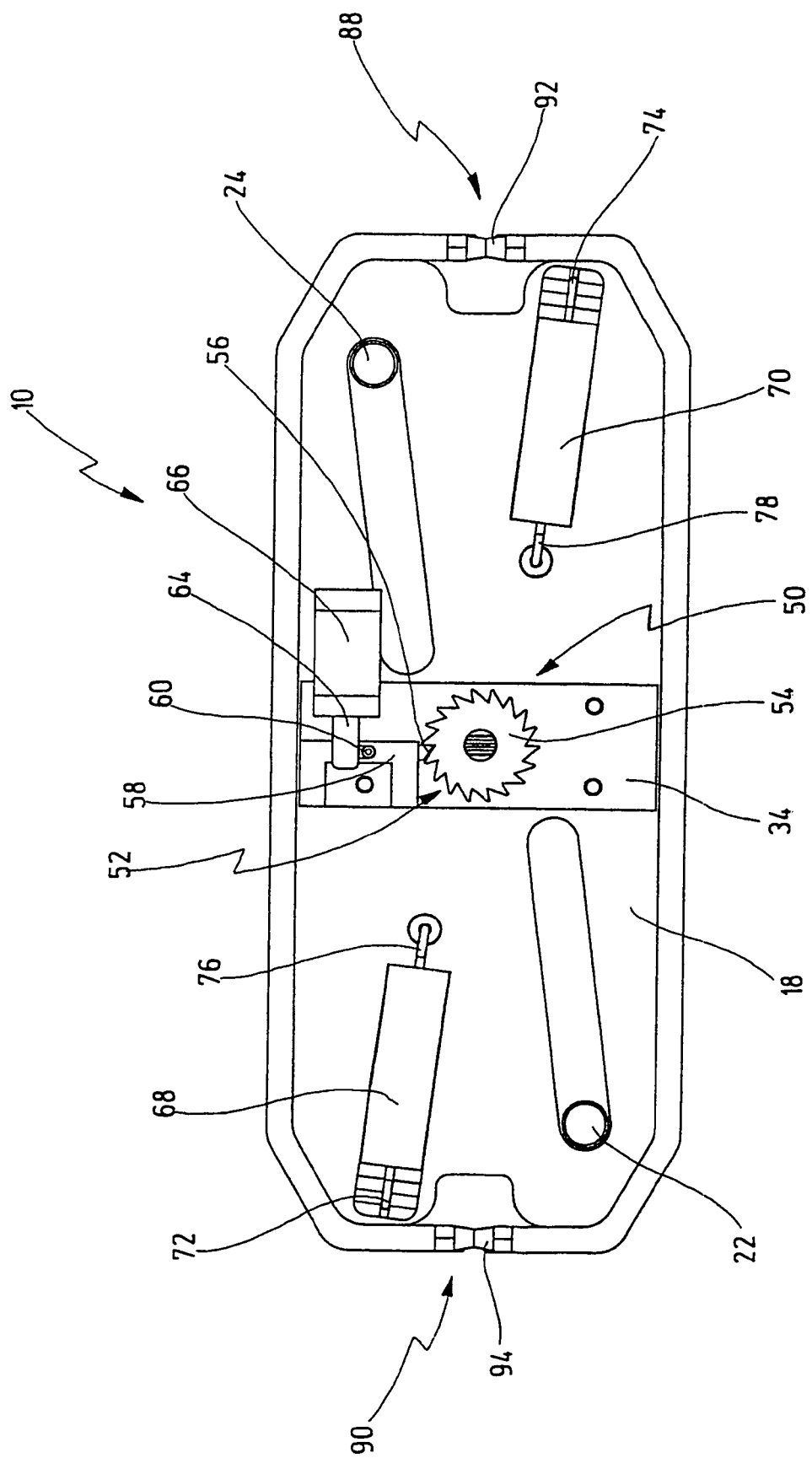
FIG. 2 shows a plan view of the device from FIG. 1, with omission of some parts of the device.

For this purpose, the device 10 comprises a locking device 50 which is configured in the form of a latching mechanism 52, which can best be seen in FIG. 2 and in FIG. 3.

The fixing element 30, which in FIGS. 2 and 3 is shown without the sleeve 46 and the control wheel 48, has a circumferentially toothed wheel 54, and a first catch element 56 which interacts with the toothed wheel 54 and which is configured in the form of a pin or peg, the latter being dimensioned and shaped in such a way that it is able to engage substantially with a form fit between two teeth of the toothed wheel 54, as is shown in FIG. 2.

The toothed wheel 54 is connected fixedly in terms of rotation to the slotted portion 38 of the fixing element 30.

The catch element 56 is arranged longitudinally displaceably in a guide 58 and is connected fixedly to an actuating element 60 for moving the catch element 56 into and out of engagement with the toothed wheel 54.

In the assembled state of the device 10, the actuating element 60 protrudes through the top plate 20 through an oblong hole 62 in the latter.

The latching mechanism 52 can also be secured against undesired unlocking. For this purpose, the first catch element 56, which as has already been mentioned is movable in its longitudinal direction, can be locked when it is in engagement with the toothing of the toothed wheel 54, as is shown in FIG. 2. To lock the first catch element 56, a second catch element 64 is provided which can be shifted into the path of movement of the first catch element 56. The second catch element 64 is configured in the form of a peg which is fixedly connected to an actuating element 66 in order to move the second catch element 64 into the path of movement of the first catch element 56 or out of said path. The actuating element 66 is configured in the form of a slide which is displaceable in the directions of a double arrow 68, i.e. the actuating element 66 is movable in directions transverse to the movement of the first catch element 56.

In the operating position of the second catch element 64 shown in FIG. 2, it blocks the movement of the actuating element 60 and therefore of the first catch element 56, so that the latter, in the operating position of the second catch element 64 shown in FIG. 2, is held securely in engagement with the toothed wheel 54, as a result of which the fixing element 30 is held completely secure against rotation.

The fixing element 30 is assigned a spring for each pulling thread 12 and 14, specifically a spring 68 for the pulling thread 12 and a spring 70 for the pulling thread 14. The springs 68 and 70 are tension springs designed as helical springs which, in the illustrative embodiment shown, are enclosed by a sleeve.

The spring 68 is secured with a first end 72 on the base body 16, more precisely on the bottom plate 18 thereof, and specifically secured in an articulated manner in the illustrative embodiment shown. Correspondingly, the spring 70 is secured in an articulated manner with a first end 74 on the base body 16, i.e. on the bottom plate 18.

Figure 5:
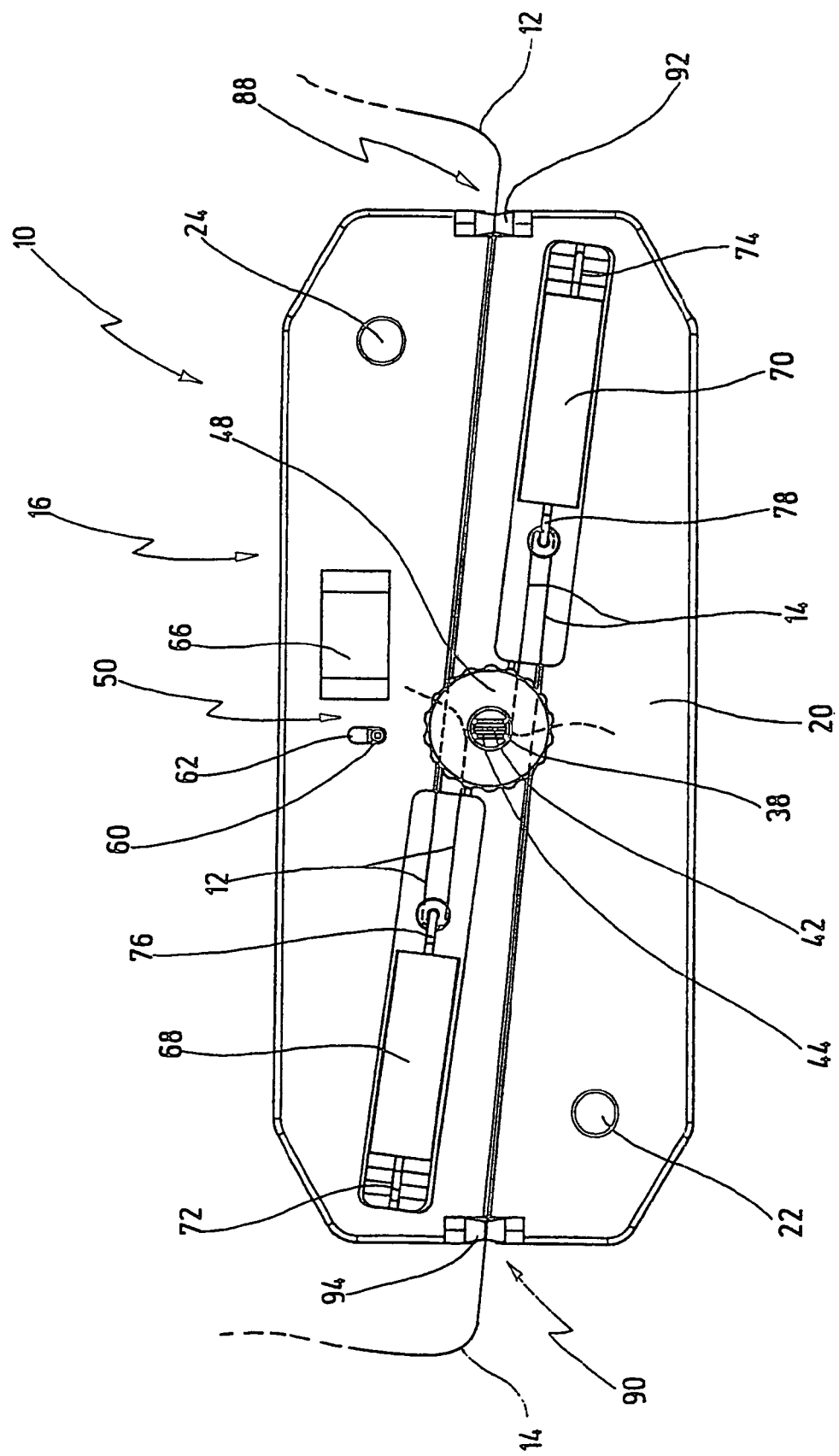
FIG. 5 shows a plan view of the device from FIG. 1, with two pulling threads additionally being indicated.

A second end 76 of the spring 68 is configured for movable connection to the pulling thread 12, and a second end 78 of the spring 70 is configured for movable connection to the pulling thread 14. Moreover, the pulling thread 12 at the second end 76 of the spring 68 is deflected toward the fixing element 30, and the pulling thread 14 at the second end 78 of the spring 70 is likewise deflected toward the fixing element 30, as is shown in FIG. 5. Guide rollers 80 and 82 that are movable, i.e. movable in rotation, are arranged respectively at the second ends 76 and 78.

Figure 1:
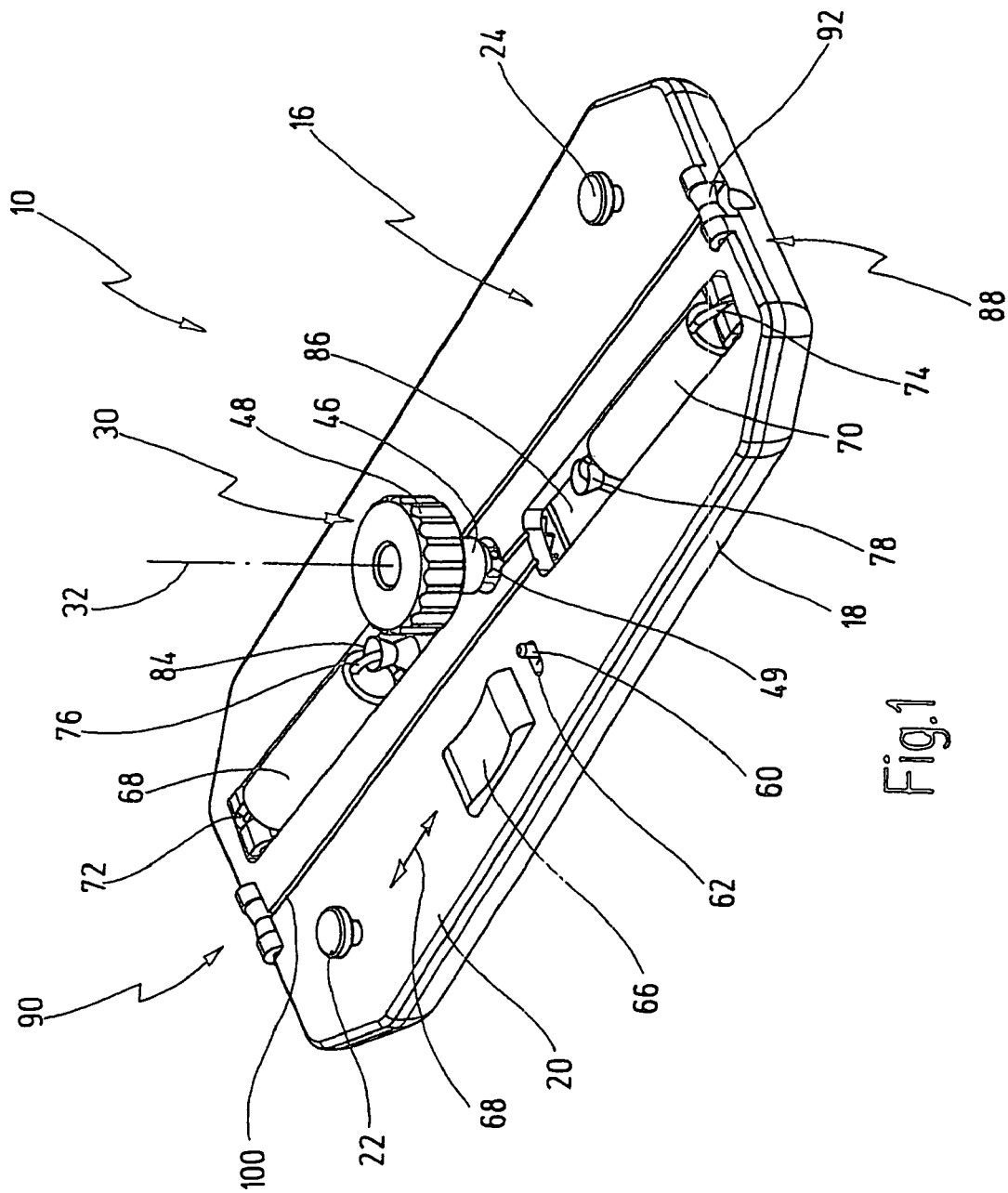
FIG. 1 shows a device for fixing and tensioning at least one pulling thread for applying a neovagina, in a perspective view from above.

As will be seen in particular from FIG. 1, oblong recesses 84 and 86 are present in the top plate 20 of the base body 16, into which recesses the springs 68 and 70 come to lie, respectively, such that they are accessible from the outside when the top plate 20 and the bottom plate 18 are joined together. To take account of the possible extension of the springs 68 and 70, the recesses 84 and 86 are made longer than the springs 68 and 70 in their relaxed state.

A feed point is provided on the base body 16, one for the pulling thread 12 and one for the pulling thread 14, namely a feed point 88 for the pulling thread 12 (see FIG. 5) and a feed point 90 for the pulling thread 14.

The feed points 88 and 90, which ensure a defined feed of the pulling threads 12 and 14 into the device 10 and thus a defined tensile force direction for the pulling threads 12 and 14, each have a movable, i.e. rotationally movable, guide roller 92, 94, the pulling threads 12 and 14 being guided via the guide rollers 92 and 94, respectively, as can be seen from FIG. 5. The guide rollers 92 and 94 are secured on the bottom plate 18 of the base body 16 (see FIG. 3). The feed points 88 and 90 are now arranged in relation to the springs 68 and 70 and to the fixing element 30 in such a way that the pulling thread 12 runs from the feed point 88 first past the fixing element 30 to the second end 76 of the spring 68, is deflected there through approximately 180°, and then runs to the fixing element 30. The same applies to the pulling thread 14 which runs from the feed point 90 first past the fixing element 30 to the second end 78 of the spring 70, is deflected there through approximately 180° and is then guided to the fixing element 30.

The whole arrangement of feed points 88, 90, springs 68, 70 and fixing element 30 is of a substantially mirror-symmetrical configuration with respect to the fixing element 30, i.e. the feed points 88 and 90 lie diametrically opposite one another in relation to the fixing element 30, as also do the springs 68 and 70.

By means of the just one fixing element 30, both pulling threads 12 and 14 can now be fixed and can be tensioned simultaneously and, above all, uniformly with minimal handling effort, because, after the portions 42 and 44 have been secured on the fixing element 30, all that has to be done is to turn the control wheel 48 in the clockwise direction.

Figure 6:
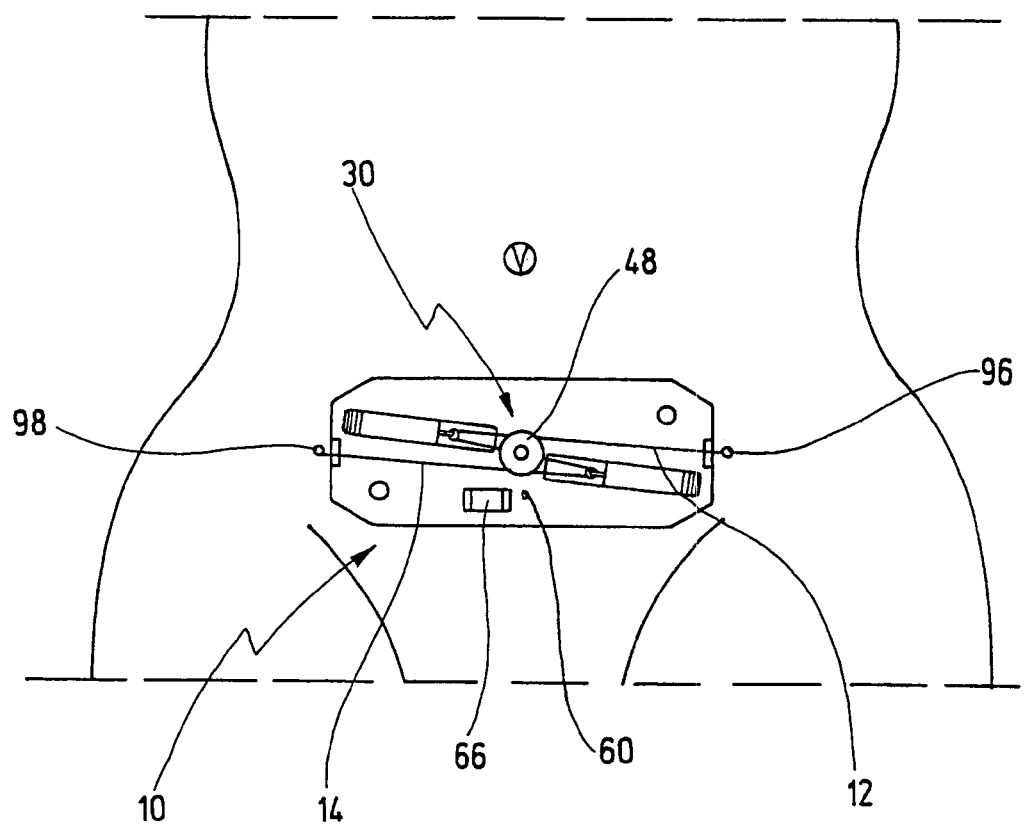
FIG. 6 shows a schematic representation illustrating the use of the device from FIG. 1 for applying a neovagina.

The use and operation of the device 10 in a method for applying a neovagina will now be described below with reference also to FIG. 6.

In the method for applying a neovagina, the two pulling threads 12 and 14, which are connected to a plastic olive (not shown) or to a phantom (not shown) intended to exert a pressure on the vaginal dimple in order to form the neovagina, are guided intraperitoneally by the plastic olive or phantom to two incisions 96 and 98 and are there routed out from the body.

The device 10 is positioned above the pubic region on the patient's abdomen, such that the feed points 88, 90 lie approximately at the level of the incisions 96, 98. The thread ends of the pulling threads 12 and 14 are now introduced via the feed point 88 and feed point 90, respectively, into the device and then, as has already been described, are routed round the second end 76 of the spring 68 and the second end 78 of the spring 70, respectively, and guided from there to the fixing element 30. The ends or portions 42 and 44 of the pulling threads 12 and 14 are then inserted into the slit 40 of the slotted portion 38 of the fixing element, the sleeve 46 with the control wheel 48 being withdrawn from the slotted portion 38. The sleeve 46 is then mounted with the control wheel 48 onto the slotted portion 38 and locked fixedly in terms of rotation.

The latching mechanism 52 is now released, or has been released before this, by the actuating element 60 for the first catch element 56 being pulled back so that the first catch element 56 disengages from the toothed wheel 54. To be able to pull the actuating element 60 back, the actuating element 66 for the second catch element 64 must also have been moved back, specifically to the left in the view in FIG. 1.

The pulling threads 12 and 14 can now be tensioned by turning the fixing element 30 in the clockwise direction, until a desired tensile stress is achieved. When the appropriate and desired tensile stress is obtained, the first catch element is brought into engagement with the toothed wheel 54 by means of the actuating element 60, and, in order to lock the latching mechanism 52, the actuating element 66 for the second catch element 64 is then displaced (to the right in FIG. 1), as a result of which the fixing element 30 is secured against turning counter to the direction of tensioning.

To increase the tension of the pulling threads 12 and 14, or also to release the tension of the pulling threads 12 and 14 if they have initially been tensioned too much, the latching mechanism simply has to be released by means of the actuating elements 66 and 60, after which the optimal tensioning force of the pulling threads 12 and 14 can be set by turning the fixing element 30 in the clockwise direction (tensioning) or in the counterclockwise direction (releasing the tension), this taking place simultaneously and therefore uniformly for the pulling threads 12 and 14.

As is shown in FIGS. 1 and 5, grooves 100 are formed in the top plate 20 of the base body 16, and the pulling threads 12 and 14 are set into these grooves 100, which means there is no danger of the pulling threads 12 and 14 getting caught.

What is claimed is:

1. A device for fixing and tensioning at least one pulling thread for applying a neovagina, comprising
a base body,
at least one fixing element arranged on said base body for fixing said at least one pulling thread and turnable about an axis of rotation for tensioning said at least one pulling thread by rotating said at least one fixing element in a first direction of rotation about said axis of rotation, and
a locking device for locking said at least one fixing element at least in a second direction of rotation opposite said first direction of rotation, and a spring assigned to said at least one fixing element, whose first end is secured on said base body, and whose second end is configured for moveable connection to said at least one pulling thread and for deflecting said at least one pulling thread toward said at least one fixing element,
wherein said at least one pulling thread is a first pulling thread, said spring is a first spring, and said at least one fixing element is designed for jointly fixing and tensioning said first pulling thread and at least one further pulling thread, and wherein a further spring for said at least one further pulling thread is arranged on said base body and, in relation to said at least one fixing element, is arranged opposite said first spring for said first pulling thread.

2. The device of claim 1, wherein said locking device has a latching mechanism for locking said fixing element in said second direction of rotation.

3. The device of claim 2, wherein said latching mechanism can be secured against undesired locking.

4. The device of claim 2, wherein said at least one fixing element has a wheel having a circumferential toothing which, in order to lock said at least one fixing element, interacts with a first catch element that can be brought into engagement with said toothing of said wheel.

5. The device of claim 4, wherein said first catch element can be locked when it is engaged with said toothing of said wheel.

6. The device of claim 5, wherein, in order to lock said first catch element, a second catch element is provided which can be shifted into a path of movement of said first catch element.

7. The device of claim 1, wherein said at least one fixing element has a slotted portion for receiving a portion of said at least one pulling thread, and a sleeve for clamping said at least one pulling thread on said at least one fixing element.

8. The device of claim 7, wherein said sleeve has a control wheel for turning said at least one fixing element.

9. The device of claim 1, wherein a moveable guide roller is arranged at said second end of said spring.

10. The device of claim 1, wherein a feed point for said at least one pulling thread is present on said base body.

11. The device of claim 10, wherein a moveable guide roller is present at said feed point.

12. The device of claim 1, wherein a feed point for said at least one pulling thread is present on said base body, and said feed point is arranged in relation to said spring and to said at least one fixing element in such a way that said at least one pulling thread first runs from said feed point past said at least one fixing element to said second end of said spring and from there to said at least one fixing element.

13. The device of claim 12, wherein said feed point is arranged in relation to said spring and to said at least one fixing element in such a way that said at least one pulling thread is deflected at said second end through approximately 180° toward said at least one fixing element.

14. The device of claim 1, wherein said at least one fixing element is designed for jointly fixing and tensioning said at least one pulling thread and at least one further pulling thread.

15. The device of claim 14, wherein a first feed point for said at least one pulling thread is present on said base body, and a second feed point for said at least one further pulling thread is provided on said base body, which second feed point is arranged, in relation to said at least one fixing element, opposite said first feed point.

16. The device of claim 1, wherein said device can be autoclaved.

* * * * *